United States Patent [19]

Millar et al.

[11] Patent Number: 5,397,560
[45] Date of Patent: Mar. 14, 1995

[54] MICROPOROUS CRYSTALLINE ALUMINOSILICATE DESIGNATED DCM-2

[75] Inventors: Dean M. Millar, Midland, Mich.; Gregg E. Lewis, Lake Jackson, Tex.; Juan M. Garcés, Midland, Mich.

[73] Assignee: The Dow Chemical Company, Midland, Mich.

[21] Appl. No.: 137,652

[22] Filed: Oct. 15, 1993

Related U.S. Application Data

[63] Continuation-in-part of Ser. No. 45,287, Apr. 6, 1993, abandoned.

[51] Int. Cl.⁶ .................................. C01B 33/34
[52] U.S. Cl. .................................. 423/700; 423/718; 502/64
[58] Field of Search ................... 423/700, 718; 502/64

[56] References Cited

U.S. PATENT DOCUMENTS

| | | |
|---|---|---|
| 2,882,244 | 4/1959 | Milton . |
| 3,123,441 | 3/1964 | Haden . |
| 3,196,106 | 7/1965 | Haden . |
| 3,216,789 | 11/1965 | Breck et al. . |
| 3,302,995 | 2/1967 | Oulton . |
| 3,322,690 | 5/1967 | Bilisoly . |
| 3,411,874 | 11/1968 | Ciric . |
| 3,459,676 | 8/1969 | Kerr . |
| 3,567,372 | 3/1971 | Duecker et al. . |
| 3,642,434 | 2/1972 | Dwyer .............................. 423/718 X |
| 3,702,886 | 11/1972 | Argauer et al. . |
| 3,754,947 | 8/1973 | Burkert et al. . |
| 3,760,062 | 9/1973 | Sand et al. ............................ 423/700 |
| 3,966,883 | 6/1976 | Vaughan et al. . |
| 4,088,739 | 5/1978 | Vaughan et al. ..................... 423/709 |
| 4,211,760 | 7/1980 | Grose et al. ........................... 423/718 |
| 4,241,036 | 12/1980 | Flanigan et al. ................. 423/718 X |
| 4,257,885 | 3/1981 | Grose et al. ........................... 210/691 |
| 4,367,924 | 1/1983 | Clark et al. ...................... 359/104 X |
| 4,560,241 | 12/1985 | Stolov et al. ...................... 359/68 X |
| 4,597,637 | 7/1986 | Ohta .......................................... 359/68 |
| 4,600,274 | 7/1986 | Morizumi ........................... 359/67 X |
| 4,639,089 | 1/1987 | Okada et al. ...................... 359/81 X |
| 4,653,862 | 3/1987 | Morizumi ........................... 359/68 X |
| 4,733,948 | 3/1988 | Kitahara ............................. 359/67 X |
| 4,766,263 | 8/1988 | Morimoto et al. ................... 585/408 |
| 4,802,743 | 2/1989 | Takao et al. ........................... 359/68 |
| 4,812,299 | 3/1989 | Wason . |
| 4,813,767 | 3/1989 | Clark et al. ...................... 359/100 X |
| 4,820,502 | 4/1989 | Rubin . |
| 4,888,120 | 12/1989 | Mueller et al. ................... 252/8.551 |
| 5,015,454 | 5/1991 | Vaughan ............................. 423/328 |

FOREIGN PATENT DOCUMENTS

| | | |
|---|---|---|
| 55-6342 | 1/1980 | Japan . |
| 60-247603 | 12/1985 | Japan . |
| 61-45226 | 3/1986 | Japan . |
| 62-150221 | 7/1987 | Japan . |
| 62-150222 | 7/1987 | Japan . |
| 2006818 | 5/1979 | United Kingdom . |

OTHER PUBLICATIONS

Breck *Zeolite Molecular Sieves* 1974 pp. 352–378.
Barrer et al. "Hydrothermal Chemistry of Silicates Part 21" *J C.S. Dalton* vol. 10 1977 (no month).
Derwent 62283U (Aug. 3, 1973) French 2,165,174.
CA 108:153914z (1988) no month.
Derwent 89-224447/31 (Jun. 23, 1989) Japanese 1160-909A.
Derwent 88-173413/25 (Nov. 23, 1987) Soviet Union 1,353,729A.
Derwent 85-294843/47 (May 15, 1985) Soviet Union 1,155,564A.
Derwent 84-003495/01 (Nov. 21, 1983) Japanese 58-199,714A.
Derwent 83-702194/27 (May 26, 1983) Japanese 58-088,119A.

*Primary Examiner*—Mark L. Bell
*Assistant Examiner*—David Sample
*Attorney, Agent, or Firm*—Marie F. Zuckerman

[57] ABSTRACT

A novel microporous crystalline aluminosilicate designated DCM-2 is disclosed. The composition, as synthesized, contains lithium cations and is represented by the oxide composition: $Li_2O \cdot Al_2O_3 \cdot 10SiO_2$. The lithium cations may be exchanged with hydrogen ions, and in the acid form the composition is useful as an adsorbent and as a catalyst for converting alkyl halides and alkanols to light hydrocarbons.

7 Claims, 1 Drawing Sheet

DEGREES 2 - THETA     * Silicon Internal Reference

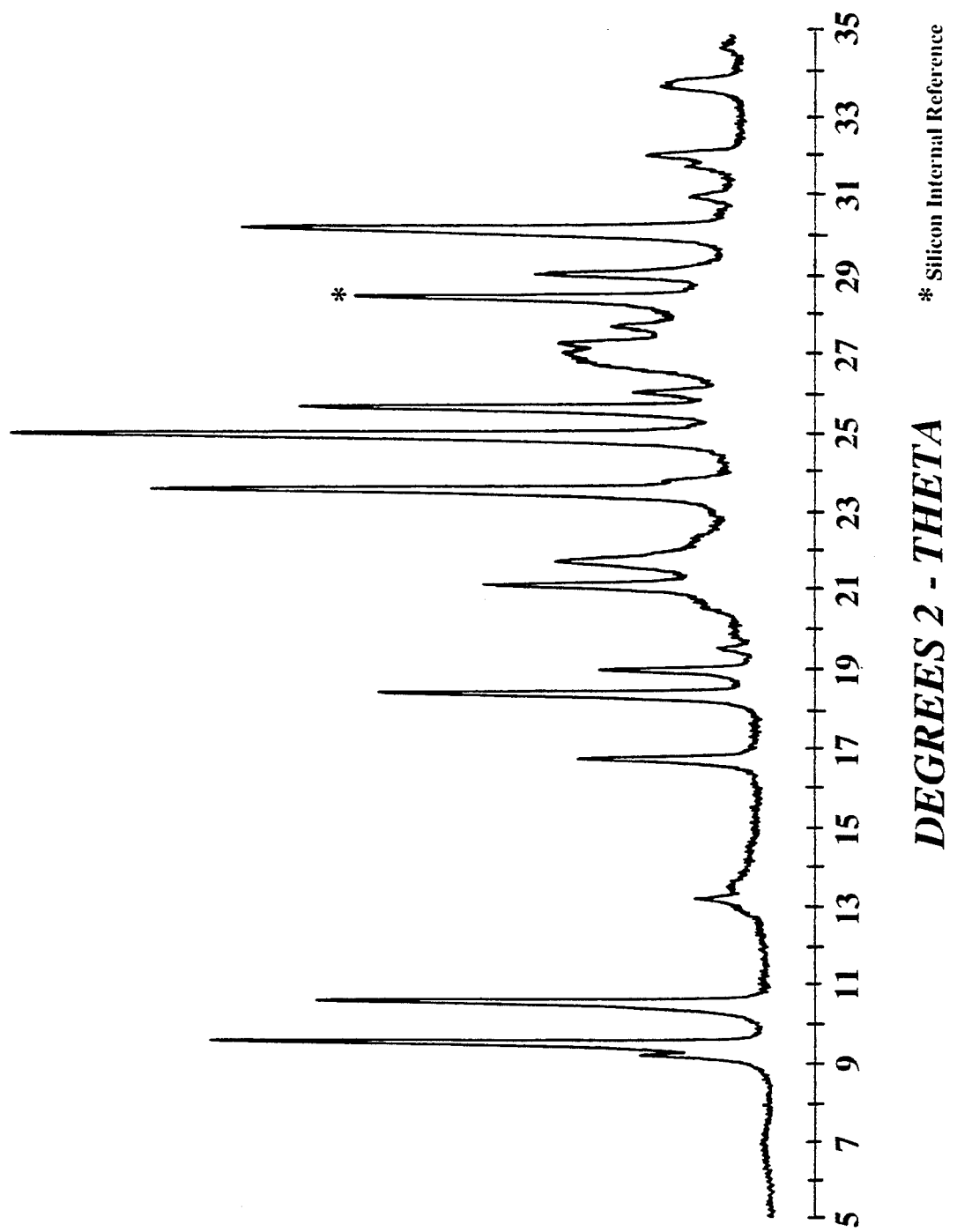

MICROPOROUS CRYSTALLINE ALUMINOSILICATE DESIGNATED DCM-2

CROSS REFERENCE TO RELATED APPLICATION

This application is a continuation-in-part of U.S. application Ser. No. 08/045,287, filed Apr. 6, 1993, now abandoned.

BACKGROUND OF THE INVENTION

In one aspect this invention pertains to microporous crystalline aluminosilicate compositions. In another aspect, this invention pertains to a process of converting alkyl halides and alkanols to olefins in the presence of a microporous crystalline aluminosilicate catalyst.

Microporous crystalline aluminosilicate compositions, otherwise known as zeolites, are useful as selective adsorbents for purifying gases and for separating mixtures of chemicals and isomers. Zeolites are also well known as shape selective catalysts for a wide variety of industrial organic processes. Illustrative of such processes are the isomerization and cracking of aliphatic hydrocarbons and the alkylation and transalkylation of aromatic compounds.

The synthesis of novel microporous crystalline aluminosilicate compositions is an ever present industry goal in view of the unique shape selective properties such compositions possess.

SUMMARY OF THE INVENTION

In one aspect this invention is a novel microporous crystalline aluminosilicate composition designated DCM-2. The novel composition is characterized by a unique X-ray diffraction pattern shown in FIG. 1 and the corresponding reflections substantially listed in Table I.

In its acid form the above-identified microporous crystalline aluminosilicate composition is useful as an adsorbent and as a catalyst for the conversion of alkyl halides and alkanols to olefins.

In a second aspect this invention is a process for converting alkyl halides and alkanols into light hydrocarbons. The process comprises contacting an alkyl halide or alkanol wherein the alkyl moiety contains from 1 to about 4 carbon atoms with a catalytic amount of the above-identified microporous crystalline aluminosilicate composition under reaction conditions such that at least one light olefin is formed.

The conversion process of this invention provides a method of preparing light olefins from feedstocks containing low molecular weight alkyl halides and alkanols. Light olefins, such as ethylene and propylene, are useful as monomers for polyolefin thermoplastics and rubbers.

DESCRIPTION OF THE DRAWINGS

FIG. 1 depicts the X-ray diffraction pattern of the novel microporous crystalline composition of this invention, designated DCM-2.

DETAILED DESCRIPTION OF THE INVENTION

As noted hereinbefore, the novel microporous crystalline aluminosilicate composition of this invention is characterized by a unique X-ray diffraction pattern, shown in FIG. 1, which distinguishes the composition from other crystalline materials. A typical diffraction pattern for this novel composition includes the reflections shown hereinafter in Table I.

TABLE I

| X-ray Diffraction Spectrum of DCM-2 | | |
|---|---|---|
| 2θ | d (Å) | 100 × I/I$_{max}$ |
| 9.1 | 9.6 | 19 |
| 9.4 | 9.3 | 86 |
| 10.5 | 8.4 | 75 |
| 13.2 | 6.6 | 12 |
| 16.7 | 5.2 | 21 |
| 18.4 | 4.8 | 45 |
| 19.0 | 4.6 | 28 |
| 19.5 | 4.5 | 10 |
| 21.1 | 4.1 | 39 |
| 21.7 | 4.0 | 46 |
| 23.5 | 3.7 | 68 |
| 24.9 | 3.5 | 100 |
| 25.7 | 3.4 | 57 |
| 27.0 | 3.3 | 40 |
| 29.0 | 3.0 | 37 |
| 30.1 | 2.9 | 91 |

The X-ray diffraction data are obtained on powder samples using copper K$_\alpha$ radiation and a computerized Philips diffractometer. The interplanar spacings, d's, are calculated in Angstrom units (Å). The relative intensities of the lines are given as 100×I/I$_{max}$ where I$_{max}$ is the strongest line above background. It should be understood that diffraction data listed for this sample as single lines may consist of multiple overlapping lines which under certain conditions, such as differences in crystallite sizes or very high experimental resolution or crystallographic changes, may appear as resolved or partially resolved lines.

As synthesized, the crystalline aluminosilicate composition of this invention typically comprises, on an anhydrous basis, oxides of lithium, aluminum and silicon in a relationship represented by the following formula:

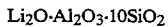

$Li_2O \cdot Al_2O_3 \cdot 10SiO_2$

The lithium ions are readily replaced with hydrogen ions to yield an acid form of the crystalline solid, designated H-DCM-2. The acid form of the crystalline solid is likewise characterized by the X-ray diffraction pattern shown in FIG. 1 and the corresponding interplanar d-spacings listed in Table I. Calcination of the lithium or acidic forms of the crystalline material to a temperature in excess of 600° C. can be conducted without significant changes in the X-ray pattern.

The crystalline aluminosilicate composition of the present invention can be prepared by hydrothermal crystallization from reactive sources of silica, alumina, and lithium ions. It has been found that the unique crystalline structure characteristic of the composition of this invention is usually not achieved if Group IA cations other than lithium ions or Group IIA cations are present in significant concentration in the reaction gel. Examples of these impurity ions include sodium, potassium, cesium and magnesium ions. Thus, any source of silica is acceptable for the preparation of the novel composition provided that the source is reactive and is essentially free of the aforementioned Group IA and IIA impurity ions. For the purposes of this invention, the term "essentially free" is defined as a concentration less than about 0.1 weight percent. Non-limiting examples of suitable sources of reactive silica include amorphous silicas, such as amorphous fumed silica, as well as, lithium silicate and silica gel. In addition, Ludox AS-40 ® brand colloidal silica, which is stabilized with ammonium ions, is a suitable source of silica. In contrast, water glass and silicic acid, both of which normally contain sodium ions, and brands of colloidal silica containing sodium ions are not suitable sources of silica for this invention. Preferably, the source of silica is amorphous fumed silica.

Any source of alumina is suitable for the preparation of the crystalline aluminosilicate composition of this invention provided that the alumina is also essentially free of the impurity ions noted hereinbefore. For example, anhydrous and hydrated forms of alumina are acceptable, but sodium aluminate is not. Preferably, the source of alumina is pseudo-boehmite alumina. The molar ratio of silica to alumina in the preparative reaction mixture can be any effective ratio which produces the composition of this invention. Typically, the $SiO_2/Al_2O_3$ molar ratio in the preparative reaction mixture ranges from about 5 to about 30. Preferably, the $SiO_2/Al_2O_3$ molar ratio ranges from about 10 to about 20.

The preparation of the novel crystalline aluminosilicate composition of this invention also requires a source of lithium ions. Lithium carbonate is particularly beneficial and is the preferred source of lithium ions.

The atomic ratio of lithium ions to silicon atoms in the preparative reaction mixture may be any which provides the crystalline aluminosilicate composition of this invention. Typically, the Li/Si ratio ranges from about 0.40 to about 1.25. Preferably, the ratio ranges from about 0.40 to about 0.80, and more preferably, from about 0.70 to about 0.80.

In a general procedure for preparing the crystalline aluminosilicate composition of this invention, the reactive sources of alumina and lithium ions are mixed with water to form an aqueous suspension. The amount of water employed in the process is any amount which is capable of providing the composition of this invention. Usually, the amount of water is sufficient to provide a $H_2O/SiO_2$ molar ratio in the range from about 9 to about 50. Preferably, the $H_2O/SiO_2$ molar ratio ranges from about 9 to about 36. The aqueous suspension of reactive alumina and lithium sources is thereafter thoroughly mixed with the reactive source of silica to form a reactive gel. An initial pH between about 10.0 and about 11.0 is preferred.

The reaction gel is placed in a suitable pressure vessel, such as a teflon-lined or stainless steel autoclave, and the vessel is heated without agitation until crystallization is complete. Typically, the temperature of heating ranges from about 190° C. to about 250° C., preferably from about 200° C. to about 225° C. The crystallization time will vary with the nature of the reaction mixture employed and the crystallization temperature. Typically, the heating time ranges from as low as about 14 days to as high as about 100 days, but preferably from about 30 days to about 70 days. X-ray diffraction peaks corresponding to the DCM-2 phase usually begin to appear after about 14 days at about 200° C. and progressively become stronger, until no further increase in peak intensity is seen after about 70 or 80 days. The reactor pressure is simply autogenous. The synthesis of the novel aluminosilicate composition may be facilitated by the addition of seed crystals to the crystallization mixture.

The lithium form of the microporous crystalline composition of this invention is recovered from the reaction gel by standard methods known to those skilled in the art. It is possible for the as-synthesized composition to contain a small amount of a dense silica phase identified as cristobalite.

In the lithium form the novel crystalline aluminosilicate has been found to adsorb and desorb water, and therefore, can be useful as an adsorbent. In this form the nitrogen-BET surface area is typically between about 1.0 and 5.0 $m^2/g$. Significantly, the lithium form of the novel crystalline aluminosilicate serves as a necessary precursor to the acid form which exhibits higher surface area and micropore volume.

The conversion of DCM-2 from the lithium form to the acid form, at least in part, is simply effected by exchanging hydrogen ions for lithium ions under acidic conditions. Typically, the lithium aluminosilicate is suspended in a dilute aqueous solution containing an inorganic acid for a time sufficient to exchange the lithium sites. Suitable acids include hydrochloric acid, sulfuric acid and nitric acid. The concentration of the acid is suitably in the range from about 1M to about 6M. The amount of acid per gram zeolite will vary depending upon the molarity of the acid solution, but preferably ranges from about 5 g to 20 g acid solution per gram zeolite. The acid exchange procedure is usually repeated at least about twice to yield the acid form of the novel aluminosilicate, designated H-DCM-2.

Advantageously, the acid form of the crystalline material has been found to be highly microporous. The nitrogen-BET surface area generally ranges from about 150 $m^2/g$ to about 250 $m^2/g$, while the total micropore area, also measured by nitrogen-BET techniques, ranges from about 160 $m^2/g$ to about 230 $m^2/g$.

The original lithium cations of the as-synthesized material can also be replaced, at least in part, by ion exchange with other metal cations, particularly, other Group IA metal ions or Group IIA metal ions. As one skilled in the art will recognize, the exchange is simply effected by suspending the crystalline material in an aqueous solution containing a salt of the exchangeable metal cation, such as a metal chloride, nitrate or sulfate.

The acid form of DCM-2 is capable of adsorbing and desorbing small molecules such as water, methanol and ethanol. In addition, the acid form of DCM-2 is capable of catalyzing the conversion of alkyl halides and alkanols into light hydrocarbons. One skilled in the art will recognize that alkyl halides include alkyl fluoride, alkyl chloride, alkyl bromide, and alkyl iodide. Alkanols include mono or dihydroxy-substituted alkanes. Typically, the alkyl moiety contains from 1 to about 4 carbon atoms, preferably, one carbon atom. Illustrative of such alkyl halides are methyl fluoride, methyl chloride, methyl bromide, methyl iodide, ethyl fluoride, ethyl chloride, ethyl bromide, and ethyl iodide, and the corresponding propyl and butyl halides. Suitable alkanols include methanol, ethanol, 1-propanol, 2-propanol, 1-butanol, 2-butanol, and 2-methyl-2-propanol. Preferably, the alkyl halide is a $C_1-C_4$ alkyl chloride, more preferably, methyl chloride. Preferably, the alkanol is methanol. The light hydrocarbons which are produced contain up to about 6 carbon atoms and include saturated and unsaturated compounds, such as, ethane, ethylene, propane, propylene, butane, butenes, pentanes, pentenes, hexanes, and hexenes. Preferably, the products are light olefins containing from 1 to about 6 carbon atoms, more preferably, ethylene and/or propylene.

The above-identified conversion process can be conducted in any reactor suitable for such a process including fixed-bed batch reactors, fixed-bed or moving-bed continuous flow reactors, and the like. Typically, the alkyl halide or alkanol is maintained in the gas phase. An inert diluent, such as nitrogen or helium gas, can be employed in the feedstream with the alkanol or alkyl halide. The concentration of alkyl halide or alkanol in the diluent typically ranges from about 10 to about 90 volume percent, preferably, from about 30 to about 70 volume percent. Any process temperature, pressure or space velocity is suitable for the process of this invention provided that a light olefin is produced as a product. The temperature usually ranges from about 250° C. to about 450° C., preferably from about 350° C. to about 425° C. Pressure can range from subatmospheric to superatmospheric, but preferably the process is run at ambient pressure. The weight hourly space velocity (WHSV) can range from values as low as 0.1 hr$^{-1}$ to values as high as 100 hr$^{-1}$. Preferably, the weight hourly space velocity ranges from about 1 hr$^{-1}$ to about 10 hr$^{-1}$.

For the purposes of this invention, the conversion is defined as the mole percentage of alkyl halide or alkanol which reacts to form products in the process of this invention. The conversion varies as a function of the specific reactants used and the process conditions, such as temperature, pressure, flow rate, and time on stream. Typically, the conversion is at least about 5 mole percent, preferably at least about 10 mole percent, more preferably, at least about 20 mole percent, and most preferably, at least about 30 mole percent. Also for the purposes of this invention, the selectivity is defined as the mole percentage of converted alkyl halide or alkanol which forms a specific product, such as an alkane or olefin. The selectivity also varies with the reactants and process conditions. Typically, the total selectivity to light hydrocarbons is at least about 10 mole percent, but can range as high as essentially 100 mole percent. Preferably, the total selectivity to olefinic products is at least about 10 mole percent, preferably, at least about 20 mole percent, more preferably, at least about 30 mole percent, and most preferably, at least about 40 mole percent.

The following examples are illustrative of the invention described hereinabove, but should not be construed to be limiting thereof.

Example 1

Preparation of DCM-2

A reaction gel having the composition 8Li$_2$O·2Al$_2$O$_3$·20SiO$_2$·720H$_2$O is prepared as follows. In a plastic beaker, Catapal B® brand boehmite alumina (1.25 g), lithium carbonate (3.25 g), and deionized water (71.32 g) are mixed and stirred vigorously. The mixture is then poured into a 2L beaker containing Aerosil® brand fumed silica (6.61 g). The resulting slurry is mixed until a homogeneous white mixture is obtained. After transferring the mixture to a suitable container, the reaction mixture is rolled with alumina milling media on a ball mill for 12 to 18 hr. The resulting reaction gel is transferred to a teflon-lined autoclave, and the reactor is heated in an oven at 200° C. for a period of 80 days. At the end of the crystallization period, a solid product is recovered by vacuum filtration, thoroughly washed with an excess of water, and thereafter dried in air at 85° C.

The as-synthesized solid contains, in addition to DCM-2, a crystalline dense silica, identified as cristobalite, and an amorphous material. Analytically pure samples of DCM-2 are obtained by finely grinding the solid product, suspending the ground solid in water (1 g solid per 50 mL water) and sonicating the suspension in an ultrasonic bath until no solids settle for 5 min after sonication has ended (about 2–5 minutes). The resulting suspension is allowed to settle for 1 day at which time a white solid has collected on the container floor and a translucent suspension remains. The liquid suspension is decanted off and discarded. The solids are resuspended in fresh water and the sonication and settling procedures are repeated. The entire process is repeated through a total of three cycles. The purified solid is collected by filtration, washed with water, and air dried at 85° C.

An X-ray diffraction pattern of the purified solid using copper K$_\alpha$ radiation reveals a crystalline composition having diffraction peaks identical to those in FIG. 1 and d-spacings identical to those shown in Table I. X-ray fluoresence indicates the presence of lithium, silicon, and aluminum as oxides in the ratio Li$_2$O·Al$_2$O$_3$·10SiO$_2$. The nitrogen-BET surface area of the solid is 3.1 m$^2$/g and the micropore area, also measured by the nitrogen-BET method, is 1.6 m$^2$/g.

Example 2

Preparation of Acid DCM-2 (H-DCM-2)

The microporous crystalline aluminosilicate prepared in Example 1 is suspended in 1M HCl (10 mL acid solution per g solid) and stirred vigorously for 2 hr at ambient temperature. Then, the solid is collected by filtration and washed with water. The entire exchange process is repeated twice more. The exchanged solid is collected by filtration, washed thoroughly with water, and dried at 85° C. in air.

An X-ray diffraction pattern of the exchanged solid using copper K$_\alpha$ radiation reveals a crystalline composition having peaks consistent with the pattern in FIG. 1 and the d-spacings in Table I. X-ray fluoresence indicates the presence of silicon and aluminum as the oxides in the ratio Al$_2$O$_3$:11·4SiO$_2$. The nitrogen-BET surface area of the solid activated at 350° C. for 16 hr is 233 m$^2$/g and the total micropore area is 222 m$^2$/g.

Example 3

Adsorption of Small Molecules

The microporous crystalline aluminosilicate H-DCM-2, prepared as in Example 2, is exposed at 24° C. to vapors of water, methanol and ethanol. The adsorptive capacities of the solid are shown hereinbelow in Table II.

TABLE II

| Adsorptive Capacities of H-DCM-2 [1] | | | |
|---|---|---|---|
| Adsorbent | Kinetic Diameter,[2] Å | Pressure, Torr | Wt. % Adsorbed |
| Methanol | 4.0 | 30.0 | 7.5 |
| Ethanol | 4.0 | 55.0 | 4.4 |
| Water | 2.6 | 22.4 | 7.9 |

[1] Temperature = 24° C.
[2] Donald W. Breck, Zeolite Molecular Sieves, John Wiley & Sons, Inc., 1974.

It is seen that H-DCM-2 can be used as an adsorbent for water, methanol and ethanol.

Example 4

Catalytic Conversion of Methyl Chloride Over H-DCM-2

The reactor is constructed of quartz with ½ outside diameter. The catalyst bed is held between a porous plug of quartz wool and a layer of catalytically inert crushed Intalox ® saddles. To assure plug flow through the reactor bed, the following conditions are imposed: (1) L/Dp 50.0, and (2) 6.0 D/Dp 15.0, wherein L is the length of the catalyst bed, Dp is the diameter of the catalyst particle, and D is the reactor diameter. The temperature of the catalyst bed is monitored by a thermocouple fixed inside the bed. The reactor is placed in a furnace constructed of two opposing Lindberg semicylindrical furnace elements.

The H-DCM-2 catalyst (0.5 g), prepared as in Example 2, is loaded into the catalyst bed, and the catalyst is pretreated at 600° C. for 2 hr under a gaseous mixture of airy helium, and nitrogen. When the pretreatment process is complete, the air stream is turned off and the catalyst is cooled to the desired reaction temperature under a helium/nitrogen flow. Methyl chloride, diluted with gaseous nitrogen, is fed to the reactor under the conditions and with the results specified in Table III. The product stream is analyzed by gas chromatography using nitrogen as an internal standard.

TABLE III

Conversion of Methyl Chloride Over H-DCM-2 [1]

| | | Mole % Selectivities | | | | | | |
|---|---|---|---|---|---|---|---|---|
| Time hr | Mole % Conv CH$_3$Cl | Methane | Ethylene | Ethane | Propylene | Propane | C$_4$'s | C$_5$'s |
| 0.83 | 22.4 | 4.4 | 13.6 | 1.7 | 23.8 | 20.2 | 32.1 | 4.2 |
| 2.15 | 16.0 | 12.7 | 18.2 | 4.0 | 24.4 | 13.2 | 24.6 | 2.9 |
| 3.46 | 6.7 | 20.1 | 21.0 | 4.7 | 25.8 | <<1 | 24.7 | 3.7 |
| 4.78 | 1.9 | 41.6 | 29.3 | <<1 | 29.0 | <<1 | <<1 | <<1 |
| 6.12 | <<1 | 93.3 | <<1 | <<1 | <<1 | <<1 | <<1 | <<1 |
| 7.43 | <<1 | 99.3 | <<1 | <<1 | <<1 | <<1 | <<1 | <<1 |

[1] Feedstream CH$_3$Cl/N$_2$ = 50/50; T = 375° C.; P = ambient; WHSV = 1 hr$^{-1}$.

It is seen that the acid form of DCM-2 catalyzes the conversion of methyl chloride to light olefins, such as ethylene and propylene. Other products include methane, ethane, and propane, as well as saturated and unsaturated C$_4$'s and C$_5$'s.

Example 5

Catalytic Conversion of Methanol Over H-DCM-2

Methanol is contacted with H-DCM-2 according to the procedure of Example 4 with the results set forth in Table IV.

TABLE IV

Conversion of Methanol Over H-DCM-2 [1]

| | | Mole % Selectivities | | | | | | |
|---|---|---|---|---|---|---|---|---|
| Time hr | % Mole Conv CH$_3$OH | Dimethyl ether | Ethylene | Ethane | Propylene | Propane | C$_4$'s | C$_5$'s |
| 1.85 | 33.9 | 100 | <<1 | <<1 | <<1 | <<1 | <<1 | <<1 |
| 3.21 | 34.3 | 80.4 | <<1 | <<1 | 10.3 | <<1 | 6.9 | 2.4 |
| 4.58 | 36.3 | 86.6 | <<1 | <<1 | 9.0 | <<1 | 2.3 | 2.1 |

[1] Feedstream N$_2$/He/CH$_3$OH = 6.7/73.3/20.0; T = 300° C.; P = ambient; WHSV = 0.94 hr$^{-1}$.

It is seen that the acid form of DCM-2 catalyzes the conversion of methanol to dimethyl ether, propylene, and C$_4$ and C$_5$ hydrocarbons. It is known that dimethyl ether is an intermediate in the conversion of methanol to light olefins. Thus, if the methanol feedstream of this process had been pretreated by conventional methods to convert a significant portion of the methanol to dimethyl ether, then the catalytic activity of H-DCM-2 could be fully utilized to enhance the conversion of dimethyl ether to light olefins, especially propylene.

What is claimed is:

1. A synthetic crystalline aluminosilicate having an x-ray diffraction pattern which includes the following reflections:

| 2Θ | d (Å) | 100 × I/I$_{max}$ |
|---|---|---|
| 9.1 | 9.6 | 19 |
| 9.4 | 9.3 | 86 |
| 10.5 | 8.4 | 75 |
| 13.2 | 6.6 | 12 |
| 16.7 | 5.2 | 21 |
| 18.4 | 4.8 | 45 |
| 19.0 | 4.6 | 28 |
| 19.5 | 4.5 | 10 |
| 21.1 | 4.1 | 39 |
| 21.7 | 4.0 | 46 |
| 23.5 | 3.7 | 68 |
| 24.9 | 3.5 | 100 |
| 25.7 | 3.4 | 57 |
| 27.0 | 3.3 | 40 |
| 29.0 | 3.0 | 37 |
| 30.1 | 2.9 | 91. |

2. The crystalline material of claim 1 comprising oxides of lithium, aluminum, and silicon in the relationship:

$$Li_2O \cdot Al_2O_3 \cdot 10SiO_2.$$

3. The crystalline material of claim 2 wherein the lithium cations are replaced at least in part with hydrogen ions, Group IIA ions, or ions of Group IA other than lithium.

4. The synthetic crystalline aluminosilicate of claim 1 having the x-ray diffraction pattern of FIG. 1 obtained by using copper K$_\alpha$ radiation.

5. A process of preparing a crystalline aluminosilicate having an x-ray diffraction pattern which includes the following reflections:

| 2Θ | d (Å) | 100 × I/I$_{max}$ |
|---|---|---|
| 9.1 | 9.6 | 19 |
| 9.4 | 9.3 | 86 |
| 10.5 | 8.4 | 75 |
| 13.2 | 6.6 | 12 |
| 16.7 | 5.2 | 21 |

-continued

| 2Θ | d (Å) | 100 × I/I$_{max}$ |
| --- | --- | --- |
| 18.4 | 4.8 | 45 |
| 19.0 | 4.6 | 28 |
| 19.5 | 4.5 | 10 |
| 21.1 | 4.1 | 39 |
| 21.7 | 4.0 | 46 |
| 23.5 | 3.7 | 68 |
| 24.9 | 3.5 | 100 |
| 25.7 | 3.4 | 57 |
| 27.0 | 3.3 | 40 |
| 29.0 | 3.0 | 37 |
| 30.1 | 2.9 | 91 | the process comprising preparing a reactive gel comprising:

(a) a source of silica which is essentially free of Group IIA metal ions and Group IA metal ions with the exception of lithium, (b) a source of alumina which is essentially free of Group IIA metal ions and Group IA metal ions with the exception of lithium, the silica to alumina molar ratio ranging from about 5 to about 30, (c) lithium carbonate in an amount such that the Li/Si atomic ratio is in the range from about 0.40 to about 1.25, and (d) water in an amount such that the molar ratio of $H_2O/SiO_2$ ranges from about 9 to about 50, and thereafter heating the reactive gel at a temperature between about 190° C. and about 250° C. for a time sufficient to produce the crystalline aluminosilicate.

6. The process of claim 5 wherein the source of silica is amorphous silica and the source of alumina is boehmite alumina.

7. The process of claim 6 wherein the reactive gel is heated at a temperature between about 200° C. and about 225° C. under autogenous pressure for a time ranging from about 14 days to about 100 days.

* * * * *

UNITED STATES PATENT AND TRADEMARK OFFICE
CERTIFICATE OF CORRECTION

PATENT NO. : 5,397,560
DATED : March 14, 1995
INVENTOR(S) : Dean M. Millar, et al It is certified that error appears in the above-indentified patent and that said Letters Patent is hereby corrected as shown below:

On the front page, Section [75] Inventors, "Dean M. Millar, Midland, Mich.; Gregg E. Lewis, Lake Jackson, Tex.; Juan M. Garcés, Midland, Mich.", should correctly read --Dean M. Millar, Midland, Mich.; Juan M. Garcés, Midland, Mich.--.

Signed and Sealed this

Sixteenth Day of January, 1996

Attest:

BRUCE LEHMAN

Attesting Officer  Commissioner of Patents and Trademarks